United States Patent
Viola

(10) Patent No.: US 8,663,096 B2
(45) Date of Patent: Mar. 4, 2014

(54) SYSTEM AND METHOD FOR RIGIDIZING FLEXIBLE MEDICAL IMPLEMENTS

(75) Inventor: Frank J. Viola, Sandy Hook, CT (US)

(73) Assignee: Covidien LP, Mansfield, MA (US)

( * ) Notice: Subject to any disclaimer, the term of this patent is extended or adjusted under 35 U.S.C. 154(b) by 1471 days.

(21) Appl. No.: 12/267,752

(22) Filed: Nov. 10, 2008

(65) Prior Publication Data

US 2009/0124857 A1    May 14, 2009

Related U.S. Application Data

(60) Provisional application No. 60/987,453, filed on Nov. 13, 2007.

(51) Int. Cl.
*A61B 1/00* (2006.01)
*A61B 19/00* (2006.01)

(52) U.S. Cl.
USPC ............ 600/141; 600/144; 600/139; 128/898

(58) Field of Classification Search
USPC .......................................... 600/139, 141, 144
See application file for complete search history.

(56) References Cited

U.S. PATENT DOCUMENTS

| | | | |
|---|---|---|---|
| 4,176,662 A | 12/1979 | Frazer | |
| 4,776,844 A | 10/1988 | Ueda | |
| 4,790,624 A | 12/1988 | Van Hoye et al. | |
| 5,114,402 A | 5/1992 | McCoy | |
| 5,143,085 A | 9/1992 | Wilson | |
| 5,211,183 A | 5/1993 | Wilson | |
| 5,337,733 A | 8/1994 | Bauerfeind et al. | |
| 5,345,937 A | 9/1994 | Middleman et al. | |
| 5,349,964 A | 9/1994 | Imran et al. | |
| 5,357,979 A | 10/1994 | Imran | |
| 5,415,633 A | 5/1995 | Lazarus et al. | |
| 5,423,771 A | 6/1995 | Imran | |
| 5,531,664 A | 7/1996 | Adachi et al. | |
| 5,531,685 A | 7/1996 | Hemmer et al. | |
| 5,759,151 A * | 6/1998 | Sturges ........................ | 600/146 |
| 5,826,776 A | 10/1998 | Schulze et al. | |
| 5,904,657 A | 5/1999 | Unsworth et al. | |
| 5,931,819 A | 8/1999 | Fariabi | |
| 5,997,526 A | 12/1999 | Giba et al. | |
| 6,278,084 B1 | 8/2001 | Maynard | |

(Continued)

FOREIGN PATENT DOCUMENTS

DE    3039551    10/1981
DE    37 07 787    9/1988

(Continued)

OTHER PUBLICATIONS

English language machine translation of DE 3707787 (Sep. 1988).*

(Continued)

*Primary Examiner* — Cherie M Stanfield

(57) ABSTRACT

A flexible steerable device comprising a plurality of interconnected segments configured to pivot relative to each other, each of the plurality of segments having a cavity disposed therein. The device also includes a flexible tube disposed within the cavities of the plurality of segments. The flexible tube includes at least one rigidizing chamber having fusible material disposed therein, wherein upon varying temperature of the fusible material, the fusible material shifts between a first state in which the flexible steerable device is flexible and a second state in which the flexible steerable device is rigidized.

24 Claims, 7 Drawing Sheets

(56) References Cited

U.S. PATENT DOCUMENTS

| | | |
|---|---|---|
| 6,323,459 B1 | 11/2001 | Maynard |
| 6,447,478 B1 | 9/2002 | Maynard |
| 6,533,752 B1 | 3/2003 | Waram et al. |
| 6,620,126 B2 | 9/2003 | Unsworth et al. |
| 6,638,268 B2 | 10/2003 | Niazi |
| 6,887,235 B2 | 5/2005 | O'Connor et al. |
| 6,939,338 B2 | 9/2005 | Waldhauser et al. |
| 7,018,346 B2 | 3/2006 | Griffin et al. |
| 7,033,318 B2 | 4/2006 | Masunishi |
| 7,066,931 B2 | 6/2006 | O'Connor et al. |
| 7,090,637 B2 | 8/2006 | Danitz et al. |
| 7,169,130 B2 | 1/2007 | Exline et al. |
| 7,291,127 B2 | 11/2007 | Eidenschink |
| 2004/0068161 A1 | 4/2004 | Couvillon, Jr. |
| 2004/0204676 A1 | 10/2004 | Anderson et al. |
| 2005/0085693 A1 | 4/2005 | Belson et al. |
| 2006/0064055 A1 | 3/2006 | Pile-Spellman et al. |
| 2006/0069346 A1 | 3/2006 | Smith et al. |
| 2006/0211979 A1 | 9/2006 | Smith et al. |
| 2007/0005041 A1 | 1/2007 | Frassica et al. |

FOREIGN PATENT DOCUMENTS

| | | | |
|---|---|---|---|
| DE | 3707787 A1 | * | 9/1988 |
| JP | 63-305836 | | 12/1988 |
| JP | 63-305836 | * | 12/1998 |
| WO | WO 02/096276 | | 12/2002 |

OTHER PUBLICATIONS

Tojo, English language translation of JP-63-305836. Dec. 13, 1988.*
Kevlar Technical Guide (DuPont, Apr. 2000).*
Hegde et al., (Polyester Fibers. Apr. 2004, found at www.engr.utk.edu/mse/Textiles/Polyester%20fiber.htm (last accessed Aug. 8, 2013).*
ISR—PCT/US2008/060394 dated: Aug. 8, 2008.
European Search Report for EP 08253690.5-2319 date of completion is Feb. 26, 2009 (3 pages).

* cited by examiner

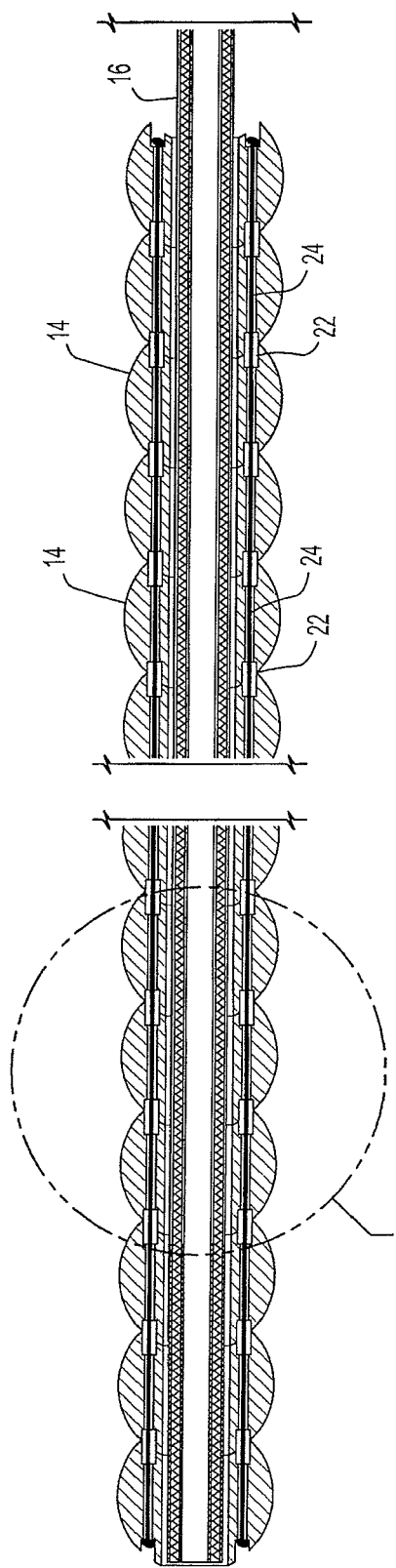
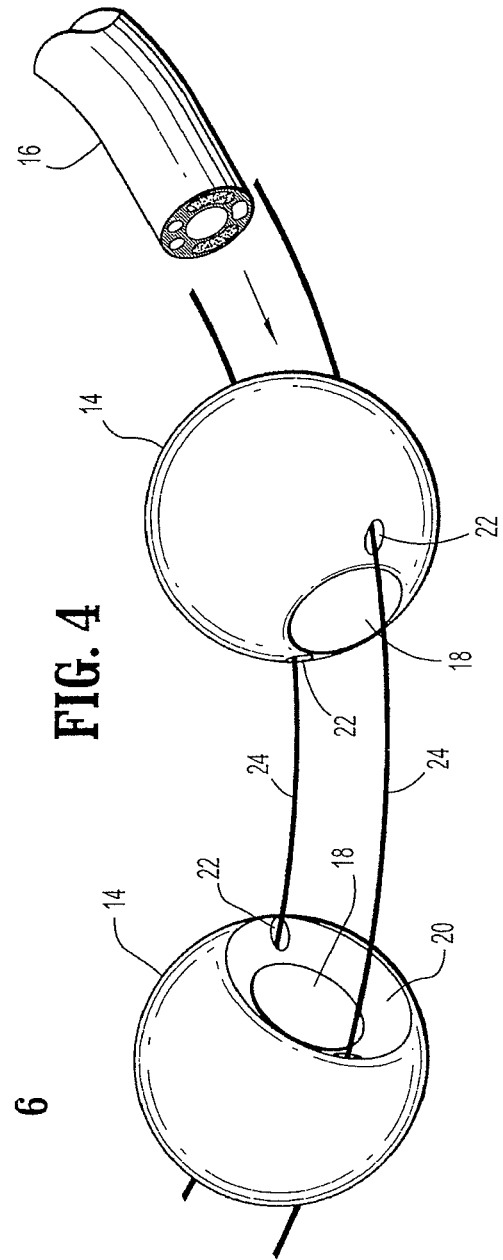
FIG. 4
FIG. 5

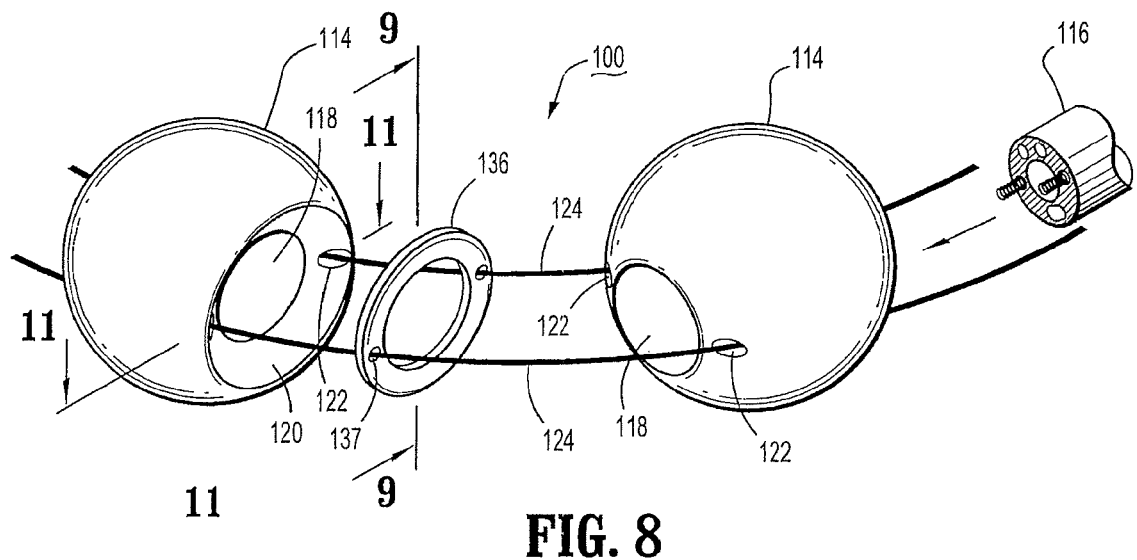
FIG. 8
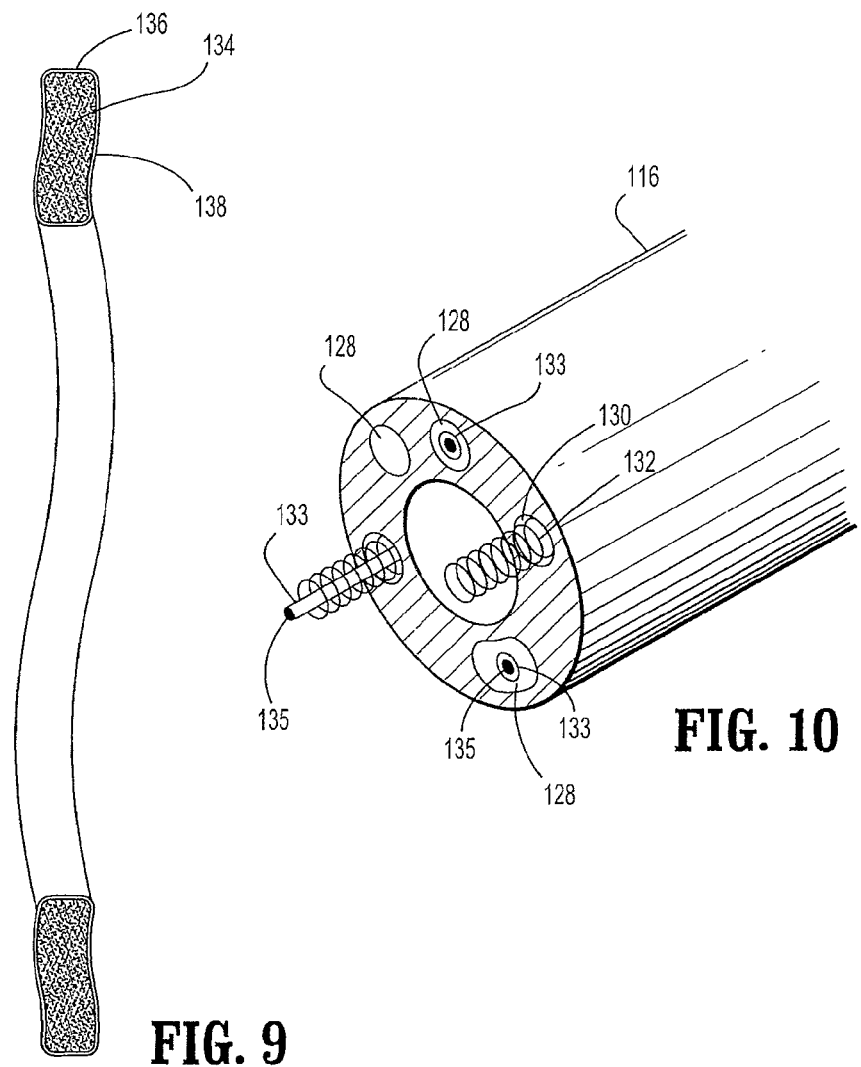
FIG. 9
FIG. 10

SYSTEM AND METHOD FOR RIGIDIZING FLEXIBLE MEDICAL IMPLEMENTS

CROSS-REFERENCE TO RELATED APPLICATIONS

This application claims the benefit of and priority to U.S. Provisional Patent Application No. 60/987,453, filed Nov. 13, 2007, the entire disclosure of which is incorporated by reference herein.

BACKGROUND

1. Technical Field

The present disclosure relates generally to flexible steerable instruments, such as steerable catheters and/or probes which are remotely operated in endoscopic, endoluminal and laparoscopic surgical procedures. In particular, the present disclosure is directed to a system and method for rigidizing a flexible steerable instrument.

2. Background of Related Art

Various minimally invasive surgical procedures utilize endoscopic, endoluminal and laparoscopic surgical techniques. These techniques generally involve insertion of surgical instruments through small incisions. One example of such surgical instruments is a flexible steerable instrument which may have a tool assembly (e.g., grasping jaws, cutting tool, camera, suction attachment, etc.) attached at a distal end of the instrument. These instruments can be navigated and steered inside the patient's body due to their flexibility. Once in position, it is often desired for the flexible steerable instruments to be held in a particular position to perform the desired tissue manipulation using the tool assembly.

Conventional flexible steerable instruments include two or more segments which are configured to pivot and/or swivel relative to each other by using one or more tensile elements running therethrough. The tensile elements are coupled to the distal segment and when the elements are tightened (e.g., pulled in the proximal direction) the segments are drawn together preventing the segments from sliding and/or pivoting due to friction forces between the segments thereby rigidizing the flexible instrument. One drawback of the conventional flexible steerable instruments utilizing tensile elements is that if an insufficient amount of tension is provided in the tensile elements, the steerable instrument may continue to swivel and/or pivot upon application of a force to the instrument. Therefore there is a need for a novel flexible steerable instrument configured to maintain its rigidity.

SUMMARY

According to one aspect of the present disclosure a flexible steerable device is disclosed. The flexible steerable device can include a plurality of interconnected segments configured to pivot relative to each other, each of the plurality of segments having a cavity disposed therein. The device can also include a flexible tube disposed within the cavities of the plurality of segments. In one embodiment, the flexible tube includes at least one rigidizing chamber having fusible material disposed therein, wherein upon varying the temperature of the fusible material, the fusible material shifts between a first state in which the flexible steerable device is flexible and a second state in which the flexible steerable device is rigidized.

According to another aspect of the present disclosure a flexible steerable device is disclosed. The flexible steerable device includes a plurality of interconnected segments configured to pivot relative to each other, each of the plurality of segments having a cavity disposed therein. The device also includes a plurality of fittings disposed between each of the plurality of interconnected segments, each of the plurality of fittings including a flexible membrane and fusible material disposed therein. The device further includes a flexible tube disposed within the cavities of the plurality of segments. The flexible tube includes at least one rigidizing chamber having a heating element, wherein the heating element is configured to vary heat applied to the fusible material in response to which the fusible material shifts between a liquid state in which the flexible steerable device is flexible and a solid state in which the flexible steerable device is rigidized.

A method for rigidizing a flexible steerable device is also contemplated by the present disclosure. The method includes the steps of providing a flexible steerable device having a plurality of interconnected segments configured to pivot relative to each other, each of the plurality of segments having a cavity disposed therein and a flexible tube disposed within the cavities of the plurality of segments. The flexible tube includes at least one rigidizing chamber having a heating element and fusible material disposed therein. The method also includes the steps of increasing heat applied to the fusible material thereby liquefying the fusible material and decreasing heat applied to the fusible material thereby solidifying the fusible material and rigidizing the flexible tube and the plurality of interconnected segments.

BRIEF DESCRIPTION OF THE DRAWINGS

The above and other aspects, features, and advantages of the present disclosure will become more apparent in light of the following detailed description when taken in conjunction with the accompanying drawings in which:

FIG. 4 is a side cross-sectional view of the flexible steerable instrument according to one embodiment of the present disclosure;

FIG. 5 is a perspective view with parts separated of the flexible steerable instrument according to one embodiment of the present disclosure;

FIG. 8 is a perspective view with parts separated of the flexible steerable instrument according to another embodiment of the present disclosure;

FIG. 9 is a side cross-sectional view of a membrane of the flexible steerable instrument according to another embodiment of the present disclosure;

FIG. 10 is a perspective view of a section of a flexible tube of the flexible steerable instrument according to another embodiment of the present disclosure;

DETAILED DESCRIPTION

Embodiments of the present disclosure will be described herein below with reference to the accompanying drawings. In the following description, well-known functions or constructions are not described in detail to avoid obscuring the present disclosure in unnecessary detail.

Figure 1:
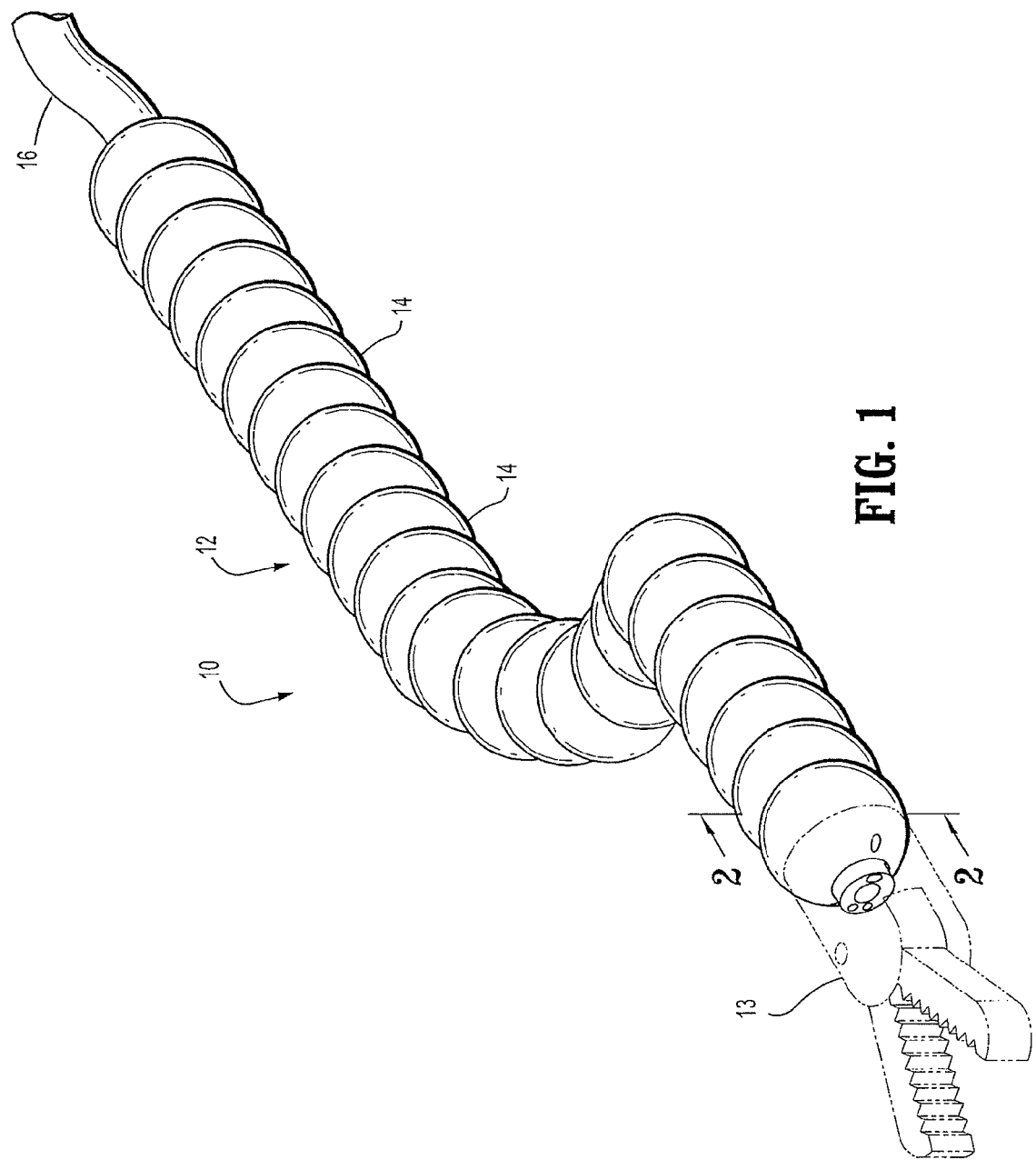
FIG. 1 is a perspective view of a flexible steerable instrument according to one embodiment of the present disclosure.

Referring to FIG. 1, a flexible steerable instrument 10 is shown. The instrument 10 includes an elongated flexible body 12 and a tool assembly 13 disposed at the distal end of the body 12. In embodiments, the tool assembly 13 may be a pair of opposing jaws as shown, e.g., graspers, pliers, etc., or other surgical tools, such as a cutting tool, e.g., scissors, dissectors, etc., and the like. Although not shown, it is envisioned that the presently disclosed instrument could be easily adapted for RF or electrical dissection or sealing. The body 12 includes a plurality of interconnected segments 14 which enclose a flexible tube 16 as shown in more detail in FIGS. 2 and 3.

Figure 2:
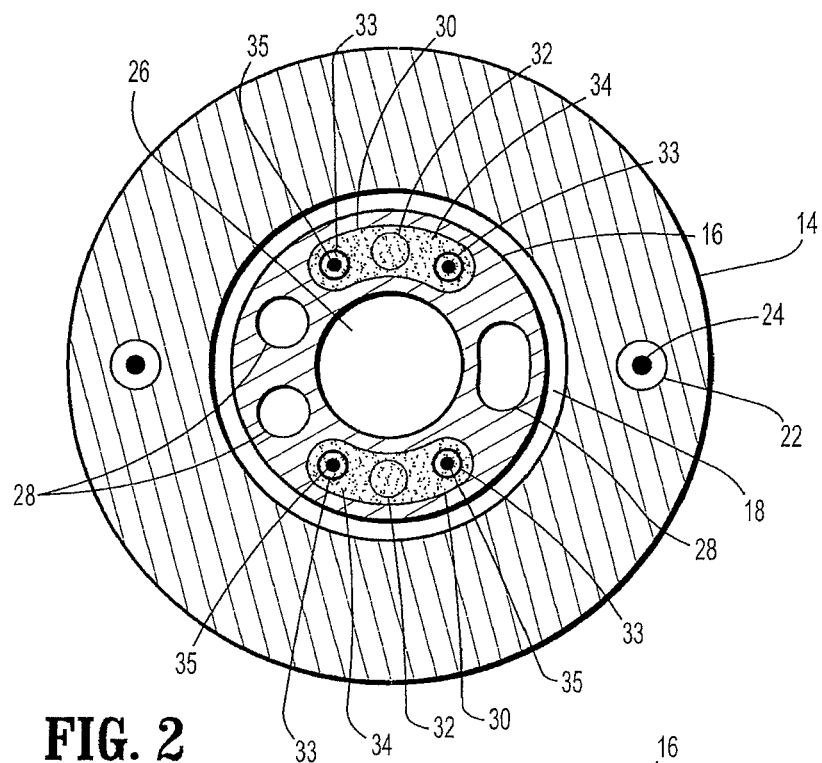
FIG. 2 is a side cross-sectional view of a segment of the flexible steerable instrument according to one embodiment of the present disclosure.

FIG. 2 shows a side cross-sectional view of the segment 14 taken along the line 2. The segment 14 has a generally spherical shape as seen in FIG. 5 and includes a cavity 18, which can be substantially cylindrical, for enclosing the tube 16. Alternately, other cavity configurations are envisioned. With reference to FIGS. 4 and 5, each of the segments 14 includes a circular depression 20 (FIG. 5) and two or more openings 22. The circular depression 20 allows the segments 14 to mechanically interface with each other by mating the proximal end of one segment 14 with the depression 20 of the immediately distal segment 14. This allows the segments 14 to pivot relative with respect to each other in a ball-joint fashion. In embodiments, the segments 14 may have a cylindrical shape with the distal and proximal ends retaining semi-spherical form to allow for ball-joint type mating between the segments 14. The segments may be formed from medical grade materials, such as stainless steel, thermoplastics, titanium, or the like.

A tensile element 24 (e.g., tinel, multi-wire cable, etc.) passes through the openings 22 and interconnects the plurality of segments 14 due to predetermined tension in the tensile element 24. The tension in the tensile element 24 is sufficient to maintain the segments 14 in physical contact with each other (e.g., proximal end of one segment 14 with depression 20 of another segment 14). Increasing tension in one of the tensile elements 24 allows for pivoting of the segments 14 in the direction in which tension is being applied. In embodiments, three or more tensile elements 24 may be used to allow for more steering control.

Figure 3:
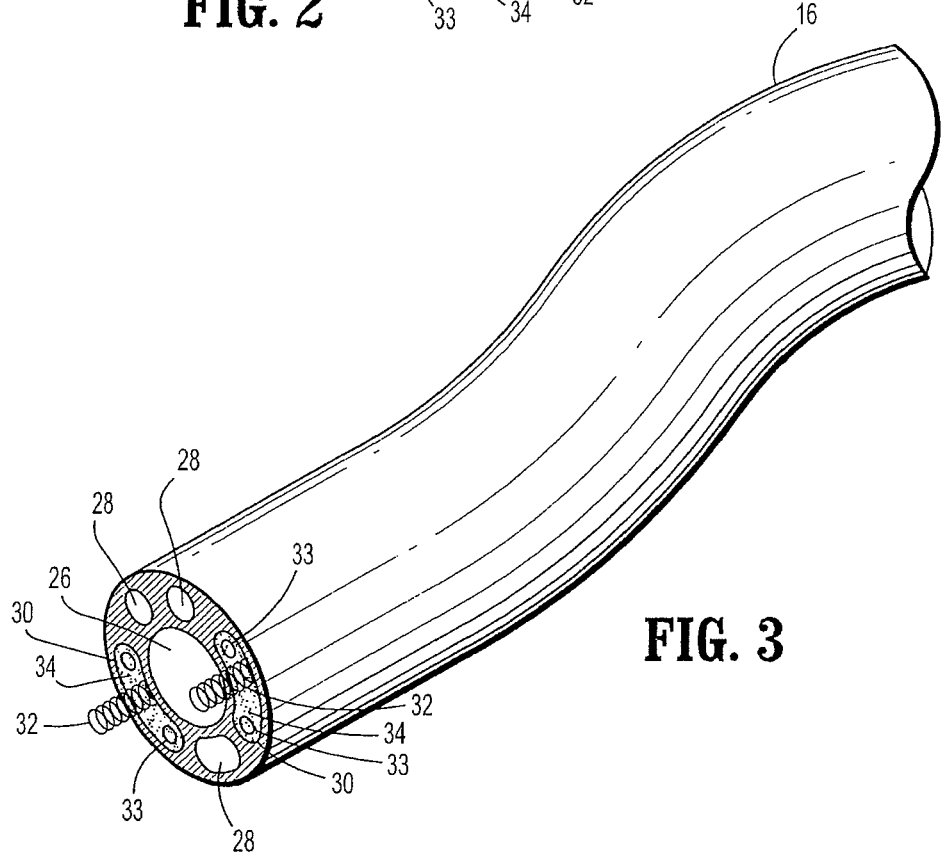
FIG. 3 is a perspective view of a section of a flexible tube of the flexible steerable instrument according to one embodiment of the present disclosure.

The tube 16 is disposed within the cavity 18 of the segments 14. With reference to FIG. 3, the tube 16 can be formed from a flexible material such as rubber, silicone rubber, and other elastomers. The tube 16 includes an endoscope port 26, one or more auxiliary ports 28 and one or more rigidizing chambers 30 formed therein. The endoscope port 26 may include cables and other actuation mechanisms for manipulating the tool assembly 13. The auxiliary port 28 may be used as a suction port or may include additional instruments, such as lights and a video camera.

The chamber 30 includes a heating element 32 and is filled with fusible material 34. The heating element 32 may be an electrical heating coil, non-electrical heat sources (e.g., heated fluid passage tube, etc.) which heats the material 34. The heating coil may be operable by any type of electrical power source, either a direct or alternating current source. In one embodiment, the chamber 30 may only be filled with the fusible material 34 and does not include the heating element 32, such that the fusible material 34 melts and solidifies in response to external temperatures (e.g., the instrument 10 being inserted into the patient).

The fusible material 34 may be any material which has a melting point at or about a predetermined threshold, such that when the material is heated above the threshold the material 34 is liquefied. In embodiments, the melting point can be any temperature above the body temperature, 37° C., allowing the material 34 to be solid when the material 34 (e.g., instrument 10) is located within the patient. The material 34 may be wax, fusible metal, fats, and the like. Thus, when the material 34 is not heated, the material 34 is solid and the instrument 10 is in rigid form since the solid material 34 prevents pivoting of the segments 14. When the material 34 is heated, the material is liquefied and the instrument 10 becomes flexible allowing for the segments 14 to pivot in the desired direction.

The fusible material 34 may be a fusible alloy containing one or more of the following metals and/or metal alloys, such as bismuth, lead, tin, antimony, indium or cadmium. During transition between liquid and solid phases, these alloys have a relatively small expansion volume allowing for their use within enclosed spaces, such as the chamber 30. When bismuth is alloyed with other metals, such as lead, tin, and cadmium, expansion of the resulting alloy is modified according to the relative percentages of bismuth and other components. Thus, bismuth alloys containing approximately 50 percent of bismuth exhibit little change of volume during solidification. Alloys containing more than this tend to expand during solidification and those containing less tend to shrink during solidification. Exemplary embodiments of the fusible alloys and their melting points are illustrated in Table (1).

TABLE (1)

|         | Bismuth | Lead  | Tin   | Antimony | Indium | Cadmium | Melting Point |
|---------|---------|-------|-------|----------|--------|---------|---------------|
| Alloy 1 | 44.7%   | 22.6% | 8.3%  | —        | 19.1%  | 5.3%    | 47° C.        |
| Alloy 2 | 49%     | 18%   | 12%   | —        | 21%    | —       | 58° C.        |
| Alloy 3 | 50%     | 26.7% | 13.3% | —        | —      | 10%     | 70° C.        |
| Alloy 4 | 42.5%   | 37.7% | 11.3% | —        | —      | 8.5%    | 70-88° C.     |
| Alloy 5 | 52.5%   | 32%   | 15.5% | —        | —      | —       | 95° C.        |
| Alloy 6 | 48%     | 28.5% | —     | 9%       | —      | 14.5%   | 103-227° C.   |
| Alloy 7 | 55.5%   | 44.5% | —     | —        | —      | —       | 124° C.       |
| Alloy 8 | 58%     | 42%   | —     | —        | —      | —       | 138° C.       |
| Alloy 9 | 40%     | —     | 60%   | —        | —      | —       | 138-170° C.   |

The chamber 30 also includes one or more coolant tubes 33 disposed therein and surrounded by the fusible material 34. The coolant tubes 33 may be formed from any type of flexible heat-resistant polymer (e.g., polyemide). The coolant tubes 33 of each chamber 30 may be interconnected at the distal end of the instrument 10 so that the coolant tubes 33 are in continuous fluid communication with each other. The coolant tubes 33 are coupled to a source of coolant fluid and a pump (not explicitly shown) which circulate the coolant fluid 35 through the coolant tubes 33. The coolant fluid 35 is supplied to the coolant tubes 33 to cool the material 34 so that the material 34 cools down and rigidizes the instrument 10.

Figure 6:
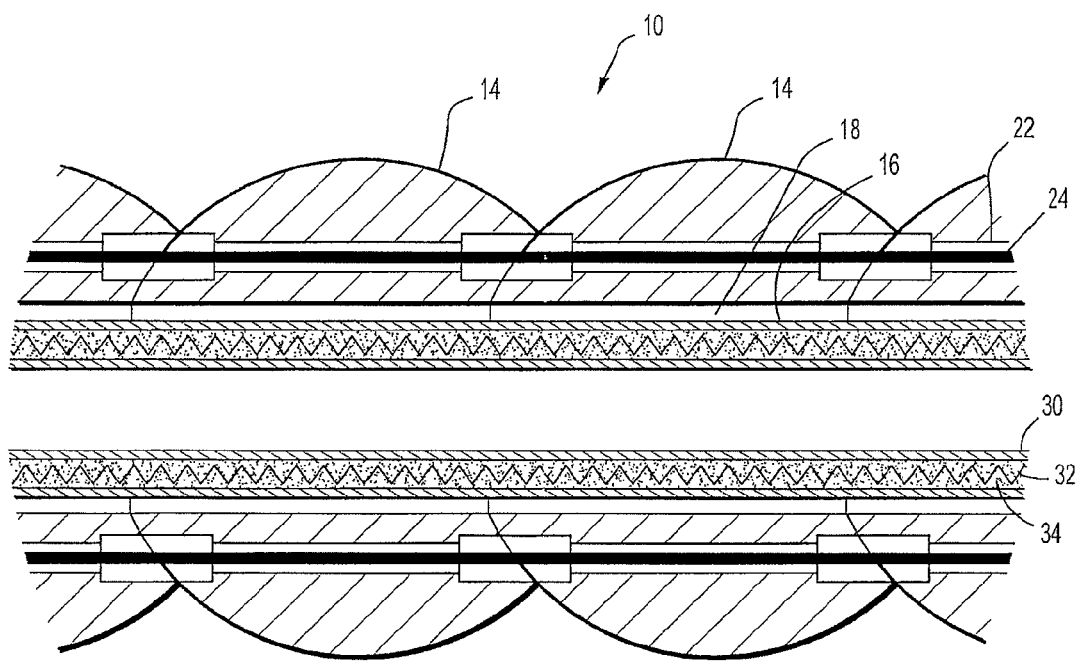
FIGS. 6 and 7 are side cross-sectional view of the flexible steerable instrument according to one embodiment of the present disclosure.
Figure 7:
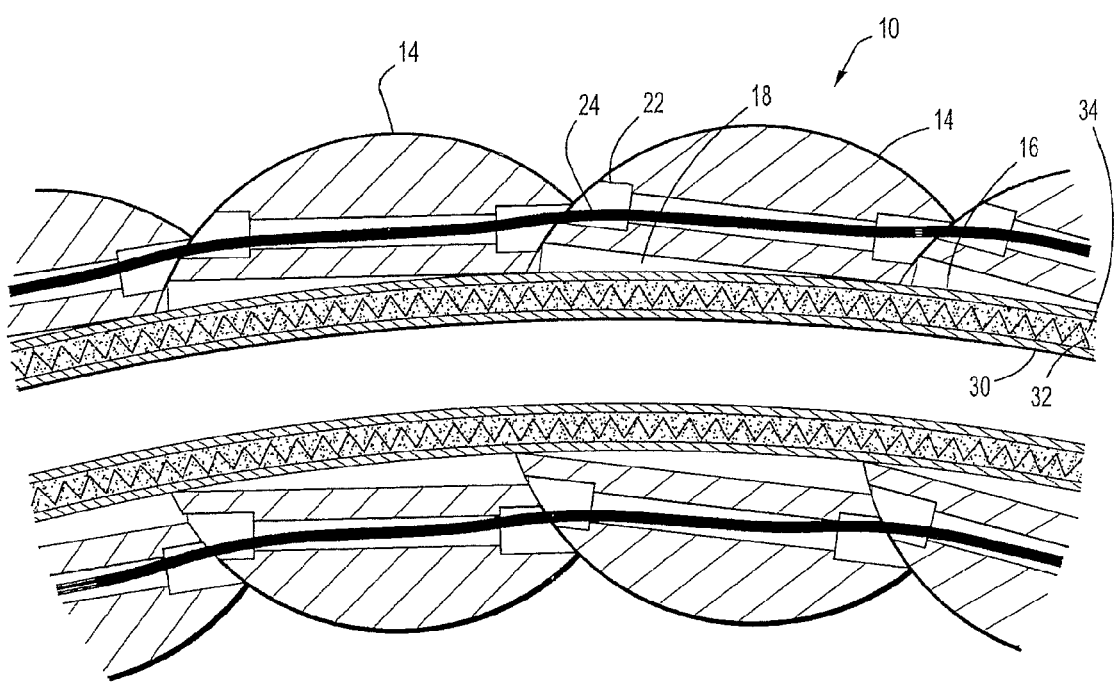

Prior to inserting the instrument 10 into a body lumen, the material 34 inside the chambers 30 is heated above the melting point via the heating elements 32. The heating element 32 is connected to a power source which is controlled by the operator when it is desired to make the instrument 10 flexible. It is envisioned that the power source may include a battery or battery pack positioned near or supported by instrument 10. Once the material 34 is heated so that the material is liquefied, the instrument 10 becomes flexible allowing for the pivoting of the segments 14 and the instrument 10 is guided to the surgical site. Guiding is accomplished by keeping the instrument 10 flexible and steering the instrument 10 by tensioning desired tensile elements 24. Once the instrument 10 is positioned at the site, the instrument 10 is rigidized by decreasing and/or shutting off the heat supplied by the heating element 32 and allowing the material 34 to cool and solidify. In one embodiment, the coolant fluid 35 is supplied to the coolant tubes 33 thereby cooling the material 34 and rigidizing the device 10. The instrument 10 can be rigidized in any desired position, either straight configuration as shown in FIG. 6 or curved configuration as shown in FIG. 7 or in any intermediate configuration. When the instrument 10 needs to be removed or relocated, heat is increased once again to make the instrument 10 flexible and the instrument 10 is guided out of the patient's body.

Figure 11:
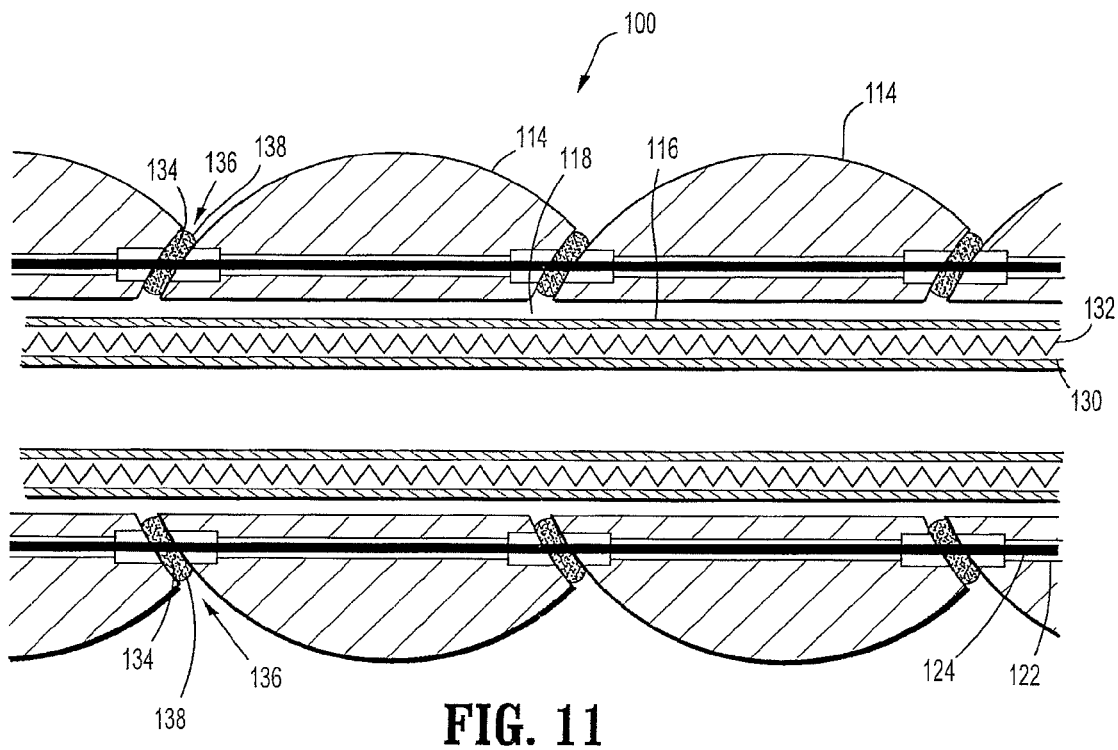
FIGS. 11 and 12 are side cross-sectional view of the flexible steerable instrument according to another embodiment of the present disclosure.
Figure 12:
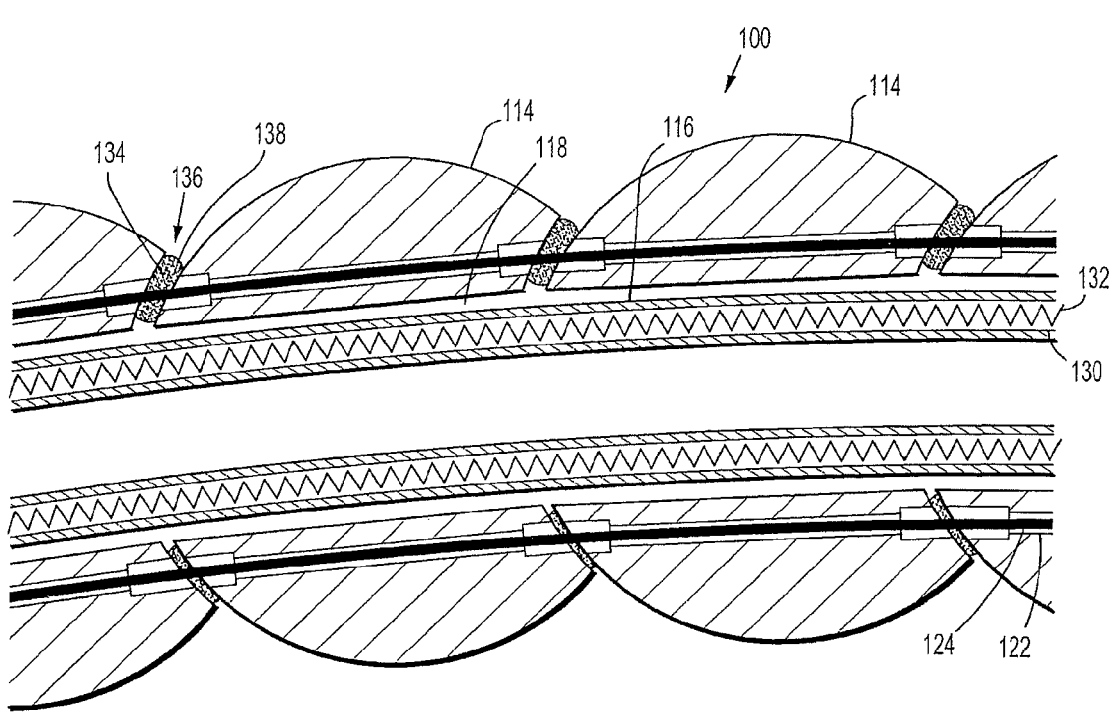

FIGS. 8-12 illustrate another embodiment of the flexible steerable instrument 100 which includes a plurality of fittings 136 disposed in between the segments 114. The instrument 100 includes a flexible tube 116 having one or more rigidizing chambers 130 and one or more auxiliary ports 128. The tube 116 is disposed within the segments 114. The fittings 136 include an outer membrane 138 and are filled with the material 134 (FIG. 9). The membrane 138 is formed from a flexible elastomer such that when the material 134 is in liquid form, the fitting 136 can be deformed as shown in FIGS. 11 and 12. The fittings 136 include openings 137 which allow for the tensile element 124 to pass therethrough. When assembled, the fittings 136 fit into the depression 122 and are squeezed between the depression 122 and the distal end of the preceding segment 114 when the tensile elements 124 are made taut.

Since the material 134 is in the fittings 136, the chamber 130 includes the heating element 132. The chamber 130 and/or the auxiliary ports 128 may include a coolant tube 133 for supplying coolant fluid 135 through the tube 116. During operation, the instrument 100 is made flexible by increasing the temperature within the chamber 130 which then liquefies the material 134 within the fittings 136. This makes the fittings 136 deformable allowing the segments 114 to pivot and/or swivel relative to each other. The instrument 100 is then guided to the surgical site in flexible form. After the instrument 100 is in the desired position the instrument 100 is rigidized by lowering and/or terminating the heat supplied by the heating elements 132 thereby cooling the material 134 within the fittings 136. This may be accomplished by pumping coolant fluid 135 through the coolant tubes 133. Once the material 134 cools, the fittings 136 become rigid and lock the segments 114 in the desired configuration as shown in FIGS. 11 and 12. FIG. 11 shows the instrument 100 rigidized in a straight configuration whereas FIG. 12 shows the instrument 100 in a curved configuration.

The chamber 130 may extend the entire length of the tube 116 or at least one portion thereof. Similarly, the fittings 136 may be disposed between only some of the segments 114 e.g., the distal-most segments, such that only a selected portion or portions of instrument 100 can be rigidized. These arrangements allow for certain portions of the instrument 100 to be rigidized, e.g., tip, while the rest of the instrument 100 can remain flexible.

Figure 13:
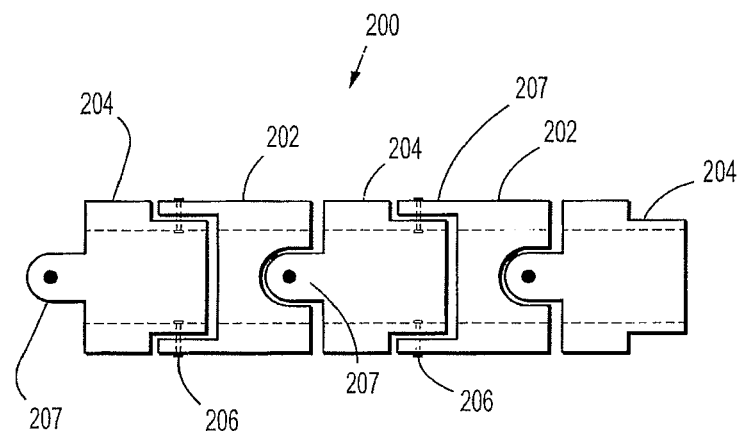
FIG. 13 is a side view of the flexible steerable instrument according to another embodiment of the present disclosure.

FIG. 13 illustrates another embodiment of the flexible steerable instrument 200. The instrument 200 includes a plurality of pivoting segments namely vertically pivoting segments 202 and horizontally pivoting segments 204. The segments 202 and 204 include one or more hinges 206 which couple the vertically pivoting segments 202 to the horizontally pivoting segments 204. The hinge 206 may include two shafts coupling the segments 202 and 204, each of the shafts connecting a tab 207 to the proximal end of the preceding segment at two points defining a single rotational axis. It is also envisioned that other types of hinges may be used, such as so-called "living hinges."

More specifically, the distal end of the vertically pivoting segment 202 is coupled to the proximal end of the horizontally pivoting segment 204 and the vertically pivoting segment 202 is adapted to hinge in a lateral direction about the hinge 206 thereof with respect to the horizontally pivoting segment 204. The distal end of the horizontally pivoting segment 204 is coupled to the proximal end of the vertically pivoting segment 202 and the horizontally pivoting segment 204 is adapted to hinge in a vertical direction about the hinge 206 thereof with respect to the vertically pivoting segment 202. This configuration provides for interspersing two types of segments having orthogonal hinges such that the consecutive segment rotates in a different direction than the previous segment thereby providing for a flexible steerable instrument 200.

Figure 14:
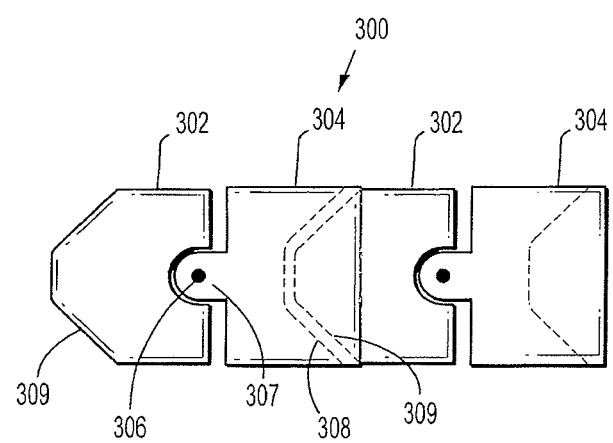
FIG. 14 is a side view of the flexible steerable instrument according to another embodiment of the present disclosure.

FIG. 14 illustrates a further embodiment of the flexible steerable instrument 300. The instrument 300 includes a plurality of rotational segments 302 separated by pivoting segments 304. Each of the rotational segments 302 is coupled to a pivoting segment 304. The pivoting segments 304 include a hinge 306 and a tab 307 which allows for pivotally coupling the pivoting segments 304 to the proximal end of the rotational segments 302. The pivoting segments 304 also include a circular depression 308 adapted to interface with a hemispherical joint 309 of the rotational segment 302 thereby mechanically interfacing the distal end of the rotational segment 302 with the proximal end of the preceding pivoting segment 304. Consequently, the instrument 300 can be flexed in any desirable direction limited only by the angle of rotation of each of the segments 302 and 304.

The flexible steering instruments 300 and 400 of FIGS. 13-14 also include one or more rigidizing chambers having heating elements disposed therein and/or coolant tubes. It is also envisioned that the instruments 300 and 400 may include the rigidizing material either directly within the rigidizing chambers or within the plurality of fittings disposed between the segments as discussed above with respect to FIGS. 1-12. In addition, the steering instruments 300 and 400 also include two or more tensile elements for guiding and steering the instruments to the desired location.

The described embodiments of the present disclosure are intended to be illustrative rather than restrictive, and are not intended to represent every embodiment of the present disclosure. Various modifications and variations can be made without departing from the spirit or scope of the disclosure as set forth in the following claims both literally and in equivalents recognized in law. For example, with respect to instrument 10, chamber 30 need not extend the entire length of tube 16 but may be provided in one or more portions of tube 16, e.g., the distal and central portions of tube 16 or just the distal portion of tube 16.

What is claimed is:

1. A flexible steerable device comprising:
    a plurality of interconnected segments configured to pivot relative to each other, each of the plurality of interconnected segments includes a cavity disposed therein; and
    a flexible tube disposed within the cavities of the plurality of segments, the flexible tube including at least one rigidizing chamber having fusible material disposed therein, the fusible material having a melting point at or above 37° C. and including a fusible alloy having bismuth and at least one metal selected from the group comprising of lead, tin, antimony, indium or cadmium, wherein upon varying temperature of the fusible material, the fusible material shifts between a first state in which the flexible steerable device is flexible and a second state in which the flexible steerable device is rigidized.

2. The flexible steerable device according to claim 1, further comprising:
    a plurality of tensile elements extending through the plurality of interconnected segments, wherein tensioning one of the plurality of tensile elements pivots the flexible steerable device.

3. The flexible steerable device according to claim 1, wherein each of the plurality of interconnected segments has a substantially spherical shape and includes a circular depression at a proximal end thereof.

4. The flexible steerable device according to claim 3, wherein each of the plurality of interconnected segments is configured to pivotally fit in the circular depression of a preceding interconnected segment.

5. The flexible steerable device according to claim 1, wherein flexible tube includes an endoscope port and at least one auxiliary port.

6. The flexible steerable device according to claim 1, wherein the flexible tube is formed from a material selected from rubber, silicone rubber, and elastomer.

7. The flexible steerable device according to claim 1, wherein the at least one rigidizing chamber extends along at least a portion of a length of the flexible tube.

8. The flexible steerable device according to claim 1, wherein the at least one rigidizing chamber further includes at least one heating element configured to vary heat applied to the fusible material.

9. The flexible steerable device according to claim 8, wherein the at least one heating element is selected from the group consisting of electrical heating coil and heated fluid passage tube.

10. The flexible steerable device according to claim 1, wherein the at least one rigidizing chamber further includes at least one coolant tube adapted to supply coolant fluid therethrough and to cool the fusible material.

11. The flexible steerable device according to claim 1, wherein the plurality of interconnected segments includes a plurality of vertically pivoting segments and a plurality of horizontally pivoting segments, each of the plurality of vertically pivoting segments being coupled to each of the plurality of the horizontally pivoting segments.

12. A flexible steerable device comprising:
    a plurality of interconnected segments configured to pivot relative to each other, each of the plurality of segments having a cavity disposed therein;
    a plurality of fittings disposed between each of the plurality of interconnected segments, each of the plurality of fittings including a flexible membrane and fusible material disposed therein, the fusible material having a melting point at or above 37° C. and including a fusible alloy having bismuth and at least one metal selected from the group comprising of lead, tin, antimony, indium or cadmium; and
    a flexible tube extending through the cavities of the plurality of segments, the flexible tube including at least one rigidizing chamber having a heating element, wherein the heating element is configured to vary heat applied to the fusible material in response to which the fusible material shifts between a liquid state in which the flexible steerable device is flexible and a solid state in which the flexible steerable device is rigidized.

13. The flexible steerable device according to claim 12, further comprising:
    a plurality of tensile elements extending through the plurality of interconnected segments, wherein tensioning one of the plurality of tensile elements pivots the flexible steerable device.

14. The flexible steerable device according to claim 12, wherein each of the plurality of interconnected segments has a substantially spherical shape and includes a circular depression at a proximal end thereof.

15. The flexible steerable device according to claim 14, wherein each of the plurality of interconnected segments is configured to pivotally fit in the circular depression of a preceding interconnected segment.

16. The flexible steerable device according to claim 12, wherein flexible tube includes an endoscope port and at least one auxiliary port.

17. The flexible steerable device according to claim 12, wherein the flexible tube and the plurality of fittings are formed from a material selected from rubber, silicone rubber, and elastomer.

18. A method for rigidizing a flexible steerable device, the method comprising the steps of:
    providing a flexible steerable device comprising:
        a plurality of interconnected segments configured to pivot relative to each other, each of the plurality of segments having a cavity disposed therein; and
        a flexible tube disposed within the cavities of the plurality of segments, the flexible tube including at least one rigidizing chamber having a heating element and fusible material disposed therein, the fusible material having a melting point at or above 37° C. and including a fusible alloy having bismuth and at least one metal selected from the group comprising of lead, tin, antimony, indium or cadmium; and
    increasing heat applied to the fusible material thereby liquefying the fusible material; and
    decreasing heat applied to the fusible material thereby solidifying the fusible material and rigidizing the flexible tube and the plurality of interconnected segments.

19. The method according to claim 18, wherein the flexible steerable device of the providing step further includes:
    a plurality of tensile elements extending through the plurality of interconnected segments, wherein tensioning one of the plurality of tensile elements pivots the flexible steerable device.

20. The method according to claim 18, wherein each of the plurality of interconnected segments of the providing step has a substantially spherical shape and includes a circular depression at a proximal end thereof.

21. The method according to claim 18, wherein each of the plurality of interconnected segments of the providing step is configured to pivotally fit in the circular depression of a preceding interconnected segment.

22. The method according to claim 18, further comprising the steps of:
increasing temperature of the fusible material above 37° C.; and
decreasing temperature of the fusible material below 37° C. thereby solidifying the fusible material and rigidizing the flexible steerable device.

23. The method according to claim 18, wherein the at least one rigidizing chamber of the providing step extends for at least a portion of the flexible tube.

24. A steerable instrument comprising:
an elongated flexible body defining one or more longitudinally extending cavities therein;
a fusible material having a melting point at or above 37° C. and including a fusible alloy having bismuth and at least one metal selected from the group comprising of lead, tin, antimony, indium or cadmium, the fusible material located within the one or more cavities, the fusible material being changeable from a solid state to a liquid state upon application of heat to the fusible material; and
a heater positioned to supply heat to the fusible material.

* * * * *